United States Patent [19]

Guillemin et al.

[11] 4,356,572

[45] Nov. 2, 1982

[54] BIODEGRADABLE IMPLANT USEABLE AS A BONE PROSTHESIS

[75] Inventors: Genevieve Guillemin; Jean-Louis Patat; Alain Patel, all of Paris, France

[73] Assignee: Etablissement Public dit: Agence Nationale de Valorisation de la Recherche (ANVAR), Neuilly sur Seine, France

[21] Appl. No.: 167,390

[22] Filed: Jul. 8, 1980

[30] Foreign Application Priority Data

Jul. 12, 1979 [FR] France .................. 79 18120

[51] Int. Cl.³ .................. A61F 1/24; A61F 5/04

[52] U.S. Cl. .................. 3/1.9; 128/92 B; 128/92 BC; 128/92 C; 128/92 D; 128/92 G; 433/201

[58] Field of Search .................. 3/1.9–1.913, 3/1; 128/92 C, 92 B, 92 CA, 92 BB, 92 G, 92 BC, 92 D, 1 R; 433/201

[56] References Cited

U.S. PATENT DOCUMENTS 3,929,971 12/1975 Roy .................. 3/1.9

*Primary Examiner*—Ronald L. Frinks
*Attorney, Agent, or Firm*—Cushman, Darby & Cushman

[57] ABSTRACT

A biodegradable bone prosthesis or implant is made of a coherent material comprising calcium carbonate in crystalline form. The prosthesis or implant is in the form of a filler or replacement part for bone substance. It can also be in the form of a pin or screw.

23 Claims, No Drawings

BIODEGRADABLE IMPLANT USEABLE AS A BONE PROSTHESIS

The present invention concerns a biodegradable implant usable as a bone prosthesis part.

More particularly, the invention concerns a biodegradable implant which can serve as a guide for new bone growth and in particular makes it possible to compensate for losses of bony substance or to replace diaphysial sections after resection.

The present invention is also aimed at facilitating anchorage of articular endoprostheses.

For the repair or replacement of broken bones or damaged articulations, the insertion of prosthetic implants of a biocompatible synthetic material having acceptable mechanical properties has already been proposed.

The difficulties encountered with procedures of fixing osteosynthetic parts by screwing or pinning have led to the use of acrylic cements like methyl methacrylate.

However, because of the use of exothermic polymerization in situ leading to a bone necrosis on the interface and because of the general toxicity of the monomer, the setting remains risky in the long term.

This is why research has tended towards new methods for attaching a prosthesis to the living bone.

There are presently two lines of research, the first being the creation of close chemical bonds between the implant and the bone, the second being biological anchoring by bony growth in prostheses made of porous material.

The broad newly formed bone surface should permit with these methods a good distribution of mechanical stress and avoid bone resorption through localized hyperpressure.

Because of the magnitude of the mechanical stress to which the bearer joints like the hip or the knee are subjected, the use of highly resistant materials is necessary.

Hence porous metals or porous ceramics have been designed and even used in man.

However, the difficulty in adjusting the size of the pores and of creating linkage channels between neighboring pores is at the source of major technical difficulties in obtaining such synthetic porous materials.

In French Pat. No. 74.11398, it was also proposed to use for creating bone implants or prostheses a synthetic material consisting of hydroxyapatite or whitlockite having a microstructure corresponding to that of the porous skeletal material of certain marine organisms, in particular echinoderms or reef-building corals.

In this French patent it is indicated that the use of material based on these natural skeletons themselves directly for the making of implants, bone substitutes or other prosthetic elements would have several drawbacks, due in particular to the low resistance and high solubility of the natural carbonates like calcite and aragonite which make up the greater part of said marine skeletal materials.

It was further thought that the prosthetic material should have, insofar as possible, a composition close to that of the bone and in particular should contain calcic phosphates which apparently favored bone growth.

This is why the authors of French Pat. No. 74.11398 sought to obtain a porous structure of the hydroxyapatite type. These synthetic porous materials are obtained by a hydrothermic chemical exchange reaction requiring the use of high temperatures and pressures.

There was therefore a prejudice against the direct utilization of the skeletons of invertebrate marine animals based on calcium carbonate.

Indeed, at first glance the hydroxyapatite-based materials seemed to have the advantage of being chemically and mineralogically very similar to normal hard human tissues and to remain stable in contact with the various physiological liquids, while the carbonate is not.

It has now been discovered, and this is the subject of the present invention, that contrary to this prejudice the utilization of a material based on calcium carbonate has many advantages.

Hence the resistance and elasticity module (Young module) of hydroxyapatite and aragonite from coral skeletons are in practice comparable when the measurements are done dry. This is no longer the case when the two materials are impregnated with a liquid, since then the hydroxyapatite-based porous structures become very crumbly, which is a definite drawback for the planned use, while the materials based on coral skeletons retain their quality of mechanical resistance.

It has also been discovered that the progressive solubility of the natural carbonates in the physiological medium does not constitute a drawback, since this resorption allows the progressive replacement of the calcium carbonate by the newly formed hard bone, and since furthermore the calcium carbonate appeared likely to favor the new bone growth more than would the calcium phosphates, contrary to another prejudice of experts in the field.

On the contrary, experience has shown that the pores of the hydroxyapatite-based materials are invaded by conjunctive tissue, but not differentiated into bone tissue.

Another advantage to utilizing the carbonates is that, because of their progressive resorption, and contrary to what happens with the nonresorbable materials, it is not necessary to implant a material having a porous structure, or in particular having a particular size of pores. Indeed, as resorption progresses the pores will necessarily reach, at a given moment, the size favorable for the new bone growth.

Finally, it has been observed that the new bone growth takes place without the formation of a fibrous capsule on the interface. The formation of such a fibrous capsule constitutes one of the drawbacks observed with classic prosthetic parts.

The present invention is thus aimed at a biodegradable prosthesis or implant made of a coherent limestone-based material.

In order for the limestone to be a sufficiently coherent material and usable according to the invention, it must contain calcium carbonate in crystalline form.

According to the invention, it is therefore possible to utilize any natural or synthetic material, nonporous or, preferably, porous, meeting this definition.

The invention is in particular aimed at a biodegradable bone prosthesis or implant characterized by the fact that it is made of a coherent material consisting of limestone in crystalline form, which preferably has a porous structure, the diameter of the pores preferably being greater or equal to 50 microns.

Indeed, the presence of a porous structure accelerates the new bone growth.

The material usable in the bone prosthesis or implant of the invention contains calcium carbonate in the form of aragonite or calcite.

Among the aragonite-based materials, we shall cite in particular those consisting of the skeleton of madrepore corals such as the porites, pocillopora, or the Favites.

In the Favites skeleton, the pores have a guiding line and consequently such a skeleton can be utilized in particular to replace diaphasial parts of long bones.

The materials based on calcite may consist in particular of echinoderm skeletons, and especially of sea urchin spines.

For example, the spines of the sea urchin Citaris can be used.

The bone prosthesis or implant according to the invention may appear in the form of a bony substance replacement or filler part, or in the form of a screw or pin.

According to another method of realization of the invention, the calcareous material as defined above is found inside hollow parts arranged in a nonresorbable endoprosthetic element, said hollow parts being in communication with the outside of said endoprosthetic element, said communications being located in an area of contact with the bony substance when the implant or prosthesis is put in place.

As calcium carbonate is progressively replaced by the newly formed bone, it is thus possible to obtain a biological anchorage for the endoprosthetic element.

Hence it is possible to make a hip prosthesis in which the femoral end is partially hollow and in which the hollow parts are filled with the calcareous material as defined above. The hollow parts are in communication with the outside of the femoral end or prosthesis through perforations, themselves filled in with said calcareous material, in the area where the femoral end is in contact with the bone after forced joining in the medullary cavity.

After the growth of new bone inside the hollow part, the prosthetic part is solidly anchored.

This anchorage avoids the use on the interface of acrylic cement, which is the major source of the loosenings observed with such prostheses.

When the limestone material used in accordance with the invention is porous, its porosity generally ranges from 30 to 80%.

The implants or prostheses of the invention are in particular filler parts for losses of bony substance, the definitive forms and sizes of which are adjusted by grinding during the operating time in order to adapt them to the particular fill-in to be made. Losses of bony substance derive in particular from traumatisms or excisions brought on by the resection of certain tumors.

The parts according to the invention can also be screws which can be used in particular for fixing the implants or prostheses of the invention, and for example for fixing the fill-in-parts defined above when the shape of the fill-in does not allow an anchorage of the filler part. These screws can also be used for fixing one edge of the fracture against the other, when the fracture lends itself to this.

These screws are made classically by drawing a shank, consisting for example of a sea urchin spine.

The utilztion of such screws, which are resorbable, makes it possible to avoid a second surgical operation which is generally necessary when nonresorbable osteosynthetic parts are used; in addition, use of the resorbable screws eliminates fatigue of the bone during the hole fill-in period after exeresis of the intrabone metal parts.

The prosthetic parts or implants of the invention may also be replacement parts intended to replace complete resections of a diaphysial segment of a long bone. Generally, one seeks to adapt the shape of the replacement part by drawing to the shape of the ends, however, the shape of said ends can be modified more favorably to the placing of the replacement part, if necessary, according to standard operating techniques.

In order to facilitate the placement of the replacement part, it is fashioned prior to the operation on the grinding wheel in order to give it a shape adapted to the resection on the one hand and to provide one of its ends with a lug intended to penetrate the medullary canal and thus assure the stability of the replacement part.

The other end can also be bevelled in order to have it penetrate the medullary canal before placement of the lug in the medullary canal at the other end of the resection. The bevelled end can then be held in place inside the medullary canal by inserting a similar corner made from the material according to the invention.

The implants or prostheses of the present invention may thus also take the shape of corners intended to hold in place other prosthetic parts, in particular replacement parts as defined above.

The prosthetic parts of the invention may also take the form of hollow articular prostheses in which the hollow parts are filled with the calcareous material as defined above.

The implants of the invention can also be used in particular as a calcic ion reserve to promote the new bone growth in the so-called bone extension technique.

When the material used to make the implants or prostheses of the invention is a piece of the skeleton of a marine animal, it is appropriate to subject it to treatments intended to clean it and eliminate organic matter likely to have harmful antigenic effects.

These operations include washing and treatment with an oxidizing solution, as for example a solution of sodium hypochlorite which makes it possible to destroy the organic matter.

Finally, the samples of calcareous material are sterilized by heat. They are then ready to be utilized surgically, it being understood that they will be fashioned during the operating time under sterile conditions.

The present invention is also aimed at the application of the implants or prostheses as defined above to the filling in or replacement of losses of bony substance or bone resections. This application can be practiced as indicated above.

The following examples illustrate the invention, without however limiting it.

EXAMPLE 1

Preliminary treatment of the material consisting of a piece of coral

For one week the piece of raw coral is abundantly rinsed in flowing water in order to rid it of the organisms inhabiting it. It is then dried in the open air, then cut with a circular saw into sections of different shapes and sizes according to needs. These sections are X-rayed on a slow-definition film in order to check the homogeneity and integrity of the skeleton's internal structure. The samples are plunged into a solution of sodium hypochlorite for 48 hours. They are again rinsed in water for 48 hours.

The samples are then sterilized in moist heat (120° C. for 30 minutes) and are then ready to be used surgically.

It is during the operating time that the sample will be fashioned to the exactly desired shape. This "modeling" or "adjusting" is done—sterilely of course—with an abrasive grinder on an electric motor. When the implant has taken on the desired shape, it is put in place. In the case of a long bone, the positioning is to be made preferably parallel to the longitudinal axis of the bone so as to assist passage of the marrow and vessels and promote and hence accelerate the new bone growth.

EXAMPLE 2

Three hip-joint prostheses have been made of Vitallium. The femoral end has the shape of a hollow cylinder, the surface of which is irregular and pierced with holes allowing communication with the hollow part which is filled with pieces of coral skeleton treated as in Example 1.

These prostheses are implanted in the femoral diaphysis of a dog. The holes for communication of the hollow part with the outside are intended to place in contact said hollow part with the medullary cavity or cortex.

After sampling at the end of three months, it was observed that bone bridges had formed through the communication holes, thus establishing a biological anchorage for the prosthesis. The calcareous material inside the hollow part of the prosthesis was not yet completely resorbed.

EXAMPLE 3

Study of filling in losses of bony substance

This experiment was carried out on adult dogs.

After exposing the femoral or cubital diaphysis, a partial loss of substance is achieved with the aid of a struck chisel. This loss of substance has the shape of a rectangular noth 20 mm long and 6 mm thick.

The calcareous material fashioned to the desired shape is inserted and held in place by an osteosynthetic plate of Vitallium fixed with screws.

By way of comparison, the behavior of filler parts made of porous hydroxyapatite according to the process in French Pat. No. 74.11398 was studied.

After selecting the observation time, the animals are killed and samples taken, fixed in a solution of formaldehyde, dehydrated by passing through alcohol, then enclosed in a polyester resin known commercially as AMBREX with a catalyst added.

After the polymerized enclosure, the block obtained is sectioned with a diamond cutting wheel.

The cuts obtained are polished on diamond abrasive disks of ever finer grain, then colored with toluidine blue at 0.2% in a buffer solution with a pH of 4.2, then rinsed. This coloring shows up the basophile elements with a blue (orthochromatic), violet (metachromasy) or purple-red (metachromasy) shade.

In addition, radiographic evolution was followed by taking shots at regular intervals.

After two weeks, the implants made with Porite skeletons showed bony spans filling in the underlying medullary space between the cortex and the implant.

Under the microscope we observe a very close contact, virtually without discontinuities, between the coral and the newly formed bone. Bone cells are visible on the coral.

After four weeks, a clear resorption of the implant is observed; it is closely surrounded by bone tissue.

A cut made at the center of the implant shows perfect continuity between the implanted material and the new bone growth, to the point that delimitation between the two materials is difficult to establish.

After eight weeks, at the center of the implantation site we find a small mass of Porites still organized, but considerably reduced, in a compact bone mass which is gradually turning into Haversian bone.

After ten weeks, resorption of the Porites is radiologically complete.

A microphotograph shows that some bone tissue in the process of mineralization has made a junction between the two edges of the fractions.

After twenty weeks, we observe complete radiological and histological disappearance of the implanted coral. The cortical bone has been completely reformed and turned into Haversian bone.

The hydroxyapatite implants gave rise to the following observations:

After two weeks, the implant is invaded by conjunctive tissue.

After four weeks, the state of the implant is radiologically identical to its initial state; histologically, the conjunctive tissue has well penetrated the free spaces; the hydroxyapatite/bone junction is irregular.

After eight weeks, the porous part of the implant is completely invaded by bone tissue. There is no obvious sign of resorption of the implant. It was not possible to observe osteoblasts on the hydroxyapatite.

EXAMPLE 4

Study of the replacement of bone resections

These replacements are made by complete resection of a diaphysial segment, the closer edge being sawed perpendicular to the longitudinal axis and the distal edge being sawed diagonally; the Porites implant is fashioned prior to the operation on the grinding wheel so as to adapt its shape to the resection and provide it with a lug on the near side of the implant intended to penetrate the medullary canal in order to assure greater stability in the replacement material.

The resected segment has roughly the shape of a parallelipiped with one base measuring 18 mm and the other 5 mm.

It is held in place by an osteosynthetic plate of Vitallium held by screws.

Post-operative retention consists of an elastoplast bandage in the case of the cubitus, and of a reinforced plaster cast in the case of a femur resection.

Samples are taken the same as in the preceding example.

After sixteen weeks, the volume of the Porites implant has considerably diminished. There is no radiological evidence of bone necrosis. There is no longer any radiological trace of the lug which initially penetrated the medullary canal and which was resorbed more quickly than the rest of the implant.

After sixteen weeks, in the case of a hydroxyapatite implant, no bone necrosis is noted. The implant is invaded by conjunctive tissue but not differentiated into bone tissue.

In conclusion, in such replacement parts hydroxyapatite is not a material that is favorable to a satisfactory restoration of bone.

On the other hand, the Porites fractions are a very progressively soluble implant of which the products of dissociation are directly usable by the bone cells forming.

In addition, we may point out that a certain number of prosthesis implants according to the invention were made in man and gave satisfactory results.

We claim:

1. A biodegradable bone prosthesis or implant made of a coherent material comprising calcium carbonate in crystalline form and being in the form of a filler part for bone substance.

2. A biodegradable bone prosthesis or implant made of a coherent material comprising calcium carbonate in crystalline form and being in the form of a replacement part for bone substance.

3. A biodegradable bone prosthesis or implant made of a coherent material comprising calcium carbonate in crystalline form and being in the form of a screw.

4. A biodegradable bone prosthesis or implant made of a coherent material comprising calcium carbonate in crystalline form and being in the form of a pin.

5. A biodegradable bone prosthesis or implant made of a coherent material comprising calcium carbonate in crystalline form and being in the form of fixation corners.

6. A biodegradable bone prosthesis or implant made of a coherent material comprising calcium carbonate in crystalline form and being in the form of a partially hollow articular prosthesis, the hollow part of which is filled with said material.

7. The biodegradable bone prosthesis or implant of claims 1, 2, 3, 4, 5 or 6 wherein said material is found inside the hollow parts of a partially hollow nonresorbable endoprosthetic element, the hollow parts being in communication with the outside of said element, said communications being located in an area of contact with the bone substance when the prosthesis or implant is put in place.

8. The biodegradable bone prosthesis or implant of claims 1, 2, 3, 4, 5 or 6 wherein said material has a porosity ranging from 30 to 80%.

9. The biodegradable bone prosthesis or implant of claim 8 wherein the diameter of the pores is at least 50 microns.

10. The biodegradable bone prosthesis or implant of claims 1, 2, 3, 4, 5 or 6 wherein said material is selected from the group consisting of aragonite and calcite.

11. The biodegradable bone prosthesis or implant of claims 1, 2, 3, 4, 5 or 6 wherein said material is sea urchin spines.

12. The biodegradable bone prosthesis or implant of claim 11 wherein said sea urchin is Citaris.

13. A process for filling in or replacing the loss of a bony substance or bone resections comprising implanting a biodegradable bone prosthesis or implant made of a coherent material comprising calcium carbonate in crystalline form.

14. The process of claim 13 wherein said material has a porous structure.

15. The process of claim 14 wherein the diameter of the pores is at least 50 microns.

16. The process of claim 13 wherein said material is selected from the group consisting of aragonite and calcite.

17. The process of claim 13 wherein said material is sea urchin spines.

18. The process of claim 13 wherein said sea urchin is Citaris.

19. The process of claim 13 wherein said material is implanted inside the hollow parts of a partially hollow nonresorbable endoprosthetic element, the hollow parts being in communication with the outside of said element, said communications being located in an area of contact with the bone substance when the prosthesis or implant is put in place.

20. A process of claim 13 wherein said material is in the form of a filler part for bone substance.

21. The process of claim 13 wherein said material is in the form of a replacement part for bone substance.

22. The process of claim 13 wherein said material is in the form of a screw.

23. The process of claim 13 wherein said material is in the form of a pin.

* * * * *